United States Patent [19]

Login et al.

[11] Patent Number: 5,262,171

[45] Date of Patent: Nov. 16, 1993

[54] PHARMACEUTICAL TABLET WITH PVP HAVING ENHANCED DRUG DISSOLUTION RATE

[75] Inventors: Robert B. Login, Oakland, N.J.; Mohammed Tazi, Marietta, Ga.; Jui-Chang Chuang, Wayne, N.J.; Rama K. Haldar, Randolph, N.J.; Dinesh Jaiswal, Butler, N.J.; Chi-San Wu, Wayne, N.J.

[73] Assignee: ISP Investments Inc., Wilmington, Del.

[21] Appl. No.: 796,999

[22] Filed: Nov. 25, 1991

[51] Int. Cl.⁵ ............ A61K 9/20; A61K 47/32; C08F 126/10; C08F 4/34

[52] U.S. Cl. ............... 424/465; 514/772.5; 514/960; 424/485; 526/264; 526/93; 526/94; 526/218.1; 526/219.6; 526/227; 526/915; 526/936; 526/230.5

[58] Field of Search ............ 424/78.24, 78.32, 78.35, 424/465, 485; 514/772.5, 960; 526/93, 94, 263, 915, 936, 216, 219, 219.1, 219.5, 219.6, 227, 230.5, 264

[56] References Cited

U.S. PATENT DOCUMENTS 3,860,568  1/1975  Chabert et al. ............ 526/94
5,008,106  4/1991  Merianos et al. ............ 424/466
5,073,614 12/1991  Shih et al. ............ 526/258
5,082,910  1/1992  Tazi ............ 526/227

Primary Examiner—Edward Webman
Attorney, Agent, or Firm—Walter Katz; Marilyn J. Maue; Joshua J. Ward

[57] ABSTRACT

A pharmaceutical tablet is provided herein having an effective dissolution rate. The tablet contains a pharmaceutically-active ingredient and a substantially linear, i.e. non-crosslinked K-30 to K-120 PVP as a binding agent. The PVP used herein is made by an initiated polymerization process in which vinyl pyrrolidone monomer is polymerized in the presence of an initiator which produces a linear PVP polymerization, i.e. is a poor hydrogen abstractor of PVP polymer backbones, which would produce a disadvantageous crosslinked PVP product. Suitable initiators include low energy peroxyester free radical initiators, such as t-amylperoxy pivalate, an azo initiator, or a redox initiator which can perform at low temperatures.

Preferably the residual initiator level in the PVP is reduced to less than 500 ppm, thereby further precluding the possibility of crosslinking of the PVP polymer during the shelf-life of the tablet.

12 Claims, No Drawings

PHARMACEUTICAL TABLET WITH PVP HAVING ENHANCED DRUG DISSOLUTION RATE

BACKGROUND OF THE INVENTION

1. Field of the Invention

This invention relates to a pharmaceutical tablet containing polyvinyl pyrrolidone (PVP) as a binder for a pharmaceutically-active ingredient therein, and more particularly, to such tablets which dissolve readily in water to release their active material even after the product has experienced a considerable period of shelf-time.

2. Description of the Prior Art

Polyvinylpyrrolidone (PVP) also is used widely as a binding agent for pharmaceutical tablets. However, it is essential that the PVP binder itself not interfere with the normal dissolution rate of the tablet in water. Suitable PVP polymers presently used as a binder agent in pharmaceutical tablets are prepared by free radical polymerization in the presence of a free radical initiator, as described in Polymer Journal 17, No. 1, p 143-152 (1985). These free radical polymerization initiators are used in amounts of about 0.05 to 10% by weight of the monomer, and, preferably about 0.1 to 5% by weight of an initiator is required. Hydrogen peroxide, di-t-butyl peroxide, dicumyl peroxide, t-butylperoxy pivalate (TBPP) and t-butylperoxy benzoate (TBPB) are widely used free radical polymerization initiators for the preparation of PVP polymers. TBPP, for example, undergoes thermal homolysis to produce t-butoxy and t-butyl free radicals by the following mechanism shown below.

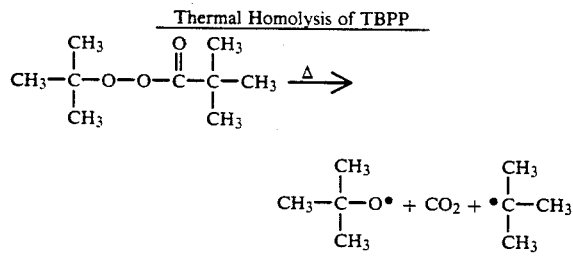

whereupon $\beta$-scission of the t-butoxy radical produces the methyl free radical:

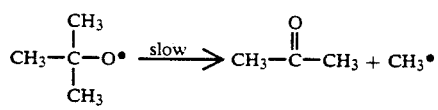

Thus, the active free radical species for initiation of free radical polymerization are:

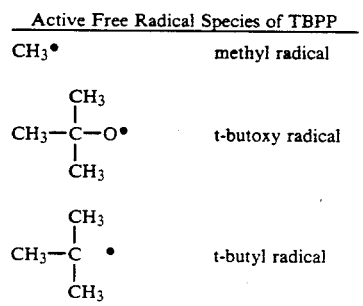

The methyl and t-butoxy free radicals, respectively, have high bond dissociation energies (BDE) of 104 and 105 kcal/mole, respectively. Therefore, these radicals can readily abstract a labile hydrogen atom from the PVP polymer to transfer the site of initiation and hence convert an otherwise linear polymer into a branched polymer. If this process is carried too far, the PVP polymer produced will have poor water solubility and/or become gels. In addition, the half-life of such TBPP initiator, i.e. the time at a given temperature to effect a loss of one-half of the perester's active oxygen content, is a lengthy 24.6 hours at 50° C. Accordingly, TBPP requires a high reaction temperature, e.g. 60°-80° C., to carry out the polymerization within a reasonable period of time. Accordingly, the choice of initiator is critical to preclude the formation of branched rather than linear PVP polymers both during polymerization and afterwards during ageing of pharmaceutical tablets containing PVP as a binding agent.

Straub, in U.S. Pat. No. 4,433,112, shows that residual initiators, especially of higher energy, can cause crosslinking of PVP even after VP is used up; therefore, there is no reason not to believe that the same thing can readily happen during polymerization. In free radical polymerization, at any instant, there is only completely formed polymer and unreacted monomer. The molecular weight of the polymer does not build with time as in polyesters. Therefore polymer is available from the onset of polymerization to be attached by initiator to cause branching and crosslinking.

Accordingly, it is an object of this invention to provide a pharmaceutical tablet containing a suitable PVP polymer as a binding agent which PVP can dissolve readily in water even after a prolonged shelf-life of the tablet.

It is another object of this invention to provide a pharmaceutical tablet using PVP as a binding agent which PVP is made by a polymerization process using a free radical initiator whose thermal homolysis reaction or redox reaction provides free radicals which because of temperature or structure are weak hydrogen abstractors, and which exhibit relatively poor electron transfer to the PVP polymer, whereby a substantially linear, non-crosslinked PVP polymer can be obtained having a high degree of water solubility even under extreme storage conditions.

SUMMARY OF THE INVENTION

A pharmaceutical tablet is provided herein containing a pharmaceutically-active ingredient and a K-30 to K-120 PVP as a binding agent, suitably about 0.5-10% by weight, preferably about 5%, which PVP is made by a free radical initiated polymerization process in which vinylpyrrolidone monomer is polymerized in the presence of a low energy peroxy radicals, such as t-amylperoxy pivalate (TAPP) as the free radical initiator, an azo initiator, or a redox initiator, at the lowest possible reaction temperatures. These named initiator materials are effective polymerization initiators for PVP polymerization, but, because of structure of the radical or the low polymerization temperature, are relatively poor hydrogen abstractors in the backbone of the PVP polymer.

Azo initiators are preferred because they generate free radicals that are of low energy. A similar effect is obtained using a lower temperature free radical initiator that has an acceptable half-life at lower temperatures because the rate expression for transfer to polymer is dependent on temperature.

Such polymerization processes of the invention are carried out at a lower temperature than similar polymerizations using related free radical initiators, which themselves are active hydrogen abstractors. Because of structure of the initiator, or because lower temperatures can be used, linear PVP polymers of high molecular weight are provided, which exhibit more rapid water solubility in use in pharmaceutical tablets. Furthermore, the low transfer to polymer property of the initiators used herein enable the residual initiator to be decomposed at elevated temperatures without causing crosslinking. For example, a PVP K-90 polymer mixture prepared in water can be post-heated at 60°–80° C. to reduce the residual initiator level to less than 500 ppm.

The tablets provided herein are particularly characterized by a rapid dissolution rate even after a prolonged shelf-life; accordingly, the PVP polymer prepared and used herein performs its binding function without an accompanying adverse side effect of a reduced dissolution rate for the active material in the tablet.

DETAILED DESCRIPTION OF THE INVENTION

In accordance with the invention, a free radical polymerization process for polymerizing vinylpyrrolidone to form PVP is provided herein. Preferably the free radical polymerization initiator is, (1) a peroxy ester which radicals are weak hydrogen abstractors, e.g. t-amylperoxy pivalate (TAPP); (2) an azo initiator, or (3) a redox catalyst. These initiators and catalysts provide low energy pathways during polymerization of VP monomer. The order of energy of polymerization, and hence the degree of crosslinking of PVP, is:

| Redox Catalyst and for peroxides TAPP | < | Azo Initiator peroxy benzoates. | < | Peroxide; Initiator |
|---|---|---|---|---|

TAPP, for example, undergoes thermal homolysis as follows:

Thermal Homolysis of TAPP

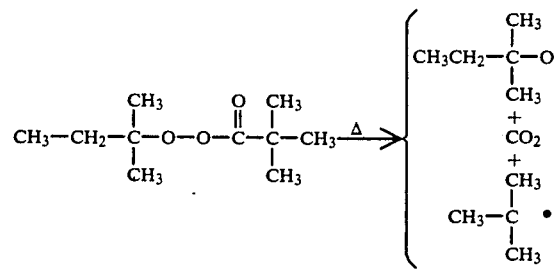

followed by β-scission of the t-amyloxy radical:

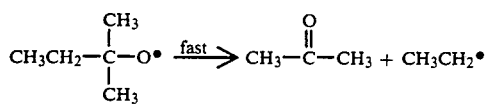

Accordingly the active free radical species of TAPP are:

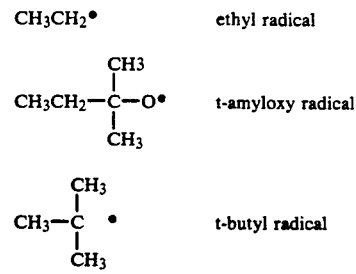

The ethyl and t-amyloxy free radicals thus produced have a BDE of only 98 kcal/mole; therefore TAPP is a relatively weak hydrogen abstractor. Thus, substantially linear PVP polymers of high molecular weight and excellent water solubility are provided using the TAPP initiator of the invention.

More particularly, as shown below, polyvinylpyrrolidone formed by free radical polymerization of vinylpyrrolidone has several active hydrogen sites, indicated by the asterisks, for hydrogen abstraction by the active free radical species of TBPP.

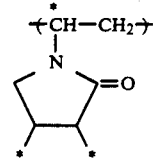

which could produce the branched and crosslinked PVP polymers shown below:

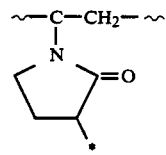

TAPP, and other low energy or poor transfer to polymer initiators, on the other hand, have only weak hydrogen abstractors or are effective for polymerization at low temperatures, and produce substantially linear PVP polymers which exhibit excellent water dissolution, even after ageing.

Furthermore, it is known that lower molecular weight polymers are produced when high polymerization temperatures or long reaction periods are required. TAPP, and azo and redox catalysts, can effect PVP polymerizations at lower temperatures, than these more active higher temperature initiators; therefore, it is possible to produce herein high molecular weight, linear PVP polymers using these defined initiators. TAPP, for example, can afford initiation and low residual peroxide residue after polymerization; furthermore it is a low energy producing radical generator with reduced capacity to extract a proton from the PVP polymer. This fact enhances the stability of the PVP polymer. Even if it contains some initiator residue, it will pass the tests used to determine tablet stability, e.g. accelerated ageing-dissolution testing. However, further heating of the formed polymer solution before drying to powder guarantees the reduction of the amount of active initiator to very low levels (<500 ppm). This post polymerization step occurs without branching or crosslinking because of the poor ability of the initiator to abstract protons from the PVP chain.

The t-amylperoxy pivalate initiator, for example, can be employed in the polymerization of vinylpyrrolidone in an amount of about 0.01% to 10% by wt. of the monomers, preferably about 0.1 to 5%.

The PVP polymers thus-produced are characterized by substantially water soluble (more linear, less branched), of stable molecular weight than PVP polymers made with more aggressive free radical initiators.

The t-amylperoxy pivalate may be obtained from the Pennwalt Corp. under their trade name of Lupersol 554M75, which is sold as a 75% by weight active solution in odorless mineral spirits.

Suitable azo-type initiators for use herein include 2,2'-azobis(isobutyronitrile), often referred to as AIBN, which is sold by Dupont under the tradename Vazo 64; 2,2'-azobis(2-methylbutanenitrile), which is Vazo 67; 2,2'-azobis(2,4-dimethylpentanenitrile), often referred to as ABVN, which is Vazo 52; 1,1'-azobis(cyclohexanecarbonitrile, Vazo 88; 2,2'-azobis(2-methylpropanimidamide) dihydrochloride; 2,2'-azobis(2-acetoxypropane; 2-tert-butylazo) isobutyronitrile; 2(tert-butylazo)-2-methylbutanenitrile; and 1-(tert-butylazo) cyclohexane-carbonitrile, sold by Pennwalt as Luazo 79, Luazo 82 and Luazo 96, respectively.

These azo-type initiators generate highly selective tertiary alkyl radicals which have a reduced propensity to attack the backbone of the polymer. This effect reduces chain branching and crosslinking and should free radicals be generated in subsequent polymer storage (even after the post polymerization heating step designed to assure very low levels of residual initiator) prevents the possibility of further reactions such as crosslinking.

A lower energy is required to generate radicals by a redox mechanism; hence the reaction is carried out at lower temperatures which does not favor transfer to polymer. If a slight excess of reducing agent is employed, no residual peroxide is available at the end.

Addition of small quantitites of reducing agents to peroxides greatly accelerates radical generation. Such Redox initiators, i.e., systems based on mixtures of oxidizing and reducing agents, initiate through the occurrence of one-electron transfer steps that form free-radical intermediates. Free-radical polymerization is used in redox mechanisms, as for example, in the system ferrous ion plus hydrogen peroxide (Fenton's reagent), since it provides an intervention of free radicals and allows their rate of formation to be measured. Many redox initiators are known and numerous "recipes" are current in polymerization technology.

Redox initiators for use herein are classified according to their solubilities (in water or organic liquids) or their mode of radical generation.

The powerfully oxidizing properties of mixtures of hydrogen peroxide and ferrous salts, discovered by Fenton in 1894, are attributed to the participation of OH and $HO_2$ radicals.

Organic peroxides or persalts such as potassium persulfate enter into similar reactions, which are essentially one-electron transfers with concomitant cleavage of the —O—O— bond.

Other transition metal ions such as $Ti^{3+}$ can enter into similar reactions.

With potassium persulfate as oxidizing agent, the analogous reactions occur. Other metal ions react with persulfates generating free radicals. Reducing agents such as those containing sulfite salts convert ferric for ferrous ion and hence propagate the decomposition of the persufate salts or organic peroxides to free radicals. The advantage is that this method of polymer initiation can occur at much lower temperatures as compared to homolytic peroxide cleavage.

For example, hydroperoxides are well-known components of redox systems and their reduction by ferrous salts has been investigated in detail. The primary step is the one-electron transfer and bond cleavage process. The product is an alkyloxy rather than a hydroxyl radical. Among the hydroperoxides are cumene, p-menthane, and p-isopropylcumene. It is common practice to add a second reducing agent such as glucose, fructose, dihydroxyacetone, or sodium formaldehyde sulfoxylate to reduce the ferric ion formed to ferrous and so keep up the rate of initiation.

Strongly reducing metal ions may enter into redox processes with compounds other than peroxide; for example, $Ti^{3+}$ can reduce hydroxylamine in acid solution to $NH_2$ radicals. Other metal ions ($Cr^{2+}$, $V^{2+}$, $Fe^{2+}$) behave similarly. These combinations are capable of initiating vinyl pyrrolidone (VP) polymerization.

In the redox systems so far discussed, the metal ion is the reducing component; however, many strongly oxidizing metal ions participate in single-electron transfer reactions, with free radical generation.

Systems in which two relatively stable salts form a redox pair may be used in the polymerizations herein. Typical oxidizing agents are potassium persulfate, potassium ferricyanide, ceric sulfate, potassium permanganate, t-butyl hydroperoxide, cumene hydroperoxide, pinane hydroperoxide, and diisopropylbenzene hydroperoxide. Reducing agents include sodium hyposulfite, sodium metabisulfite, sodium sulfide, sodium thiosulfate, and hydrazine hydrate. No transition metal derivatives are included in these examples. Both oxidizing and reducing components form free radicals, which, in principle, may initiate polymerization, although the behavior in any given system depends on the radical and monomer reactivities.

Organic peroxides may react in nonaqueous solution by redox processes. It has long been known that benzoyl peroxide can enter into relatively rapid reactions with primary, secondary, and tertiary amines.

The most familiar systems include diacyl peroxides and tertiary amines, of which benzoyl peroxide and dimethylaniline are typical. The reactants form a complex which cleaves into radicals.

In each of the above cases a reducing agent must be present to regenerate the ferrous ion. Examples would be sodium hyposulfite, sodium metabisulfite, sodium sulfide and sodium thiosulfate. Numerous recipes are aviable and are known to those skilled in the art.

Redox systems capable of free radical initiation can also be generated by the reaction of dibenzoyl peroxides and dimethylaniline, and other dialkyl peroxides and organic reducing agents such as those containing sulfinic acids, alpha-ketols, formic acid, thiols and hydrazines.

Obviously the literature of redox system is quite extensive and has recently been reviewed by for example C. H. Bamford, page 123, V. 3 of "Comprehensive Polymer Science", (1989), G. C. Eastmond et al. editors.

Redox reactions have been applied to the polymerization of PVP. Apparently the low temperature polymerization of VP and potassium persulfate reported by S. N. Trubitsyna et al. (Izv. Vuzov SSSR, Khimiya i khim. Tekhnolgiya, Vol. 22, 720 (1979) is such an example.

To achieve linearity, a source of radicals at the lowest possible temperature that efficiently promotes polymerization is theoretically the best approach to linear polymer synthesis. Hence water soluble redox reactions such as indicated below are possible.

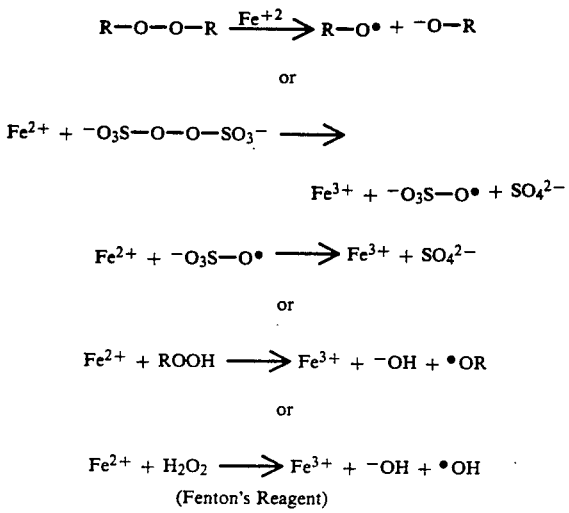

(Fenton's Reagent)

Suitable pharmaceutical tablets prepared herein are made from pharmaceutically-active materials such as acetylsalicylic acid, chloramphenicol, chloropromazine, methyl paraben, sulfathiazole trimethoprim, acetaminophen, various non-steroidal, anti-inflammatory compounds, and the like.

Suitable PVP polymers for use herein have a K-value of about 30 to 120, preferably 85 to 95.

The invention will now be described with reference to the following examples.

PREPARATION OF POLYVINYLPYRROLIDONE

Example 1 (TAPP, K-90)

A 2-liter reactor provided with agitation, gas inlet, condenser, and thermocouple was charged with 270 g. (2.3 moles) of non-stabilized vinylpyrrolidone monomer, which was buffered with a solution of 0.27 g. of tetrasodium pyrophosphate in 1,080 g. of deionized water. The reactor was swept clean of oxygen by admitting nitrogen gas through the inlet tube. Then the reactor was heated to 55° C. and 0.25 g. of t-amylperoxy pivalate (TAPP) was added (<0.1% by wt. of vinylpyrrolidone). The mixture was heated at 56°-59° C. for 5 hours, whereupon an additional 0.25 g. of TAPP was added and the reaction continued for 2 hours. At the end of the reaction period, the mixture was heated to 85° C. and held at this temperature until the residual peroxide level was less than 500 ppm. The product included 21% solids; the residual monomer content was 0.04%. The PVP polymer product in water thus-obtained was characterized by being substantially linear, a K-value of 90, low residual initiator level, and excellent water dissolution.

Example 2 (t-BPP, K-90)

A 5-liter reactor equipped with a turbine agitator, $N_2$ gas subsurface sparge, condenser and thermocople was charged with 3,326 g. of deionized water, 1.6 g. of $NH_4OH$ (38% $NH_3$) and 2-5 ppm EDTA. Then was added 1,000 g. of unstabilized vinyl pyrrolidone, the mixture sparged with $N_2$ and heated to 55° C. t-Butylperoxy pivalate (0.23 g.) was added and the polymerization begun as evidenced by a modest exotherm. The temperature was maintained at 70°-80° C. for 2 hours and residual VP measured. Small charges of t-BPP (0.05 grams) were added as required to bring the residual VP to below 0.1%. Thereafter the temperature was raised to 85° C. until residual peroxide was less than 500 ppm; the solids level was 17-18%. The aqueous solution then was dried and milled to provide the polymer in powder form.

Example 3 (t-BPP, K-90)

A 12-liter four-necked flask equipped with mecahnical stirrer, reflux condenser, thermometer, and glass stopper was purged with nitrogen for 15 minutes. 1150 g. of vinylpyrrolidone and 3850 g. of distilled water were then charged and a poitive nitrogen pressure was maintained throughout the reaction. The reactants were heated to 55° C., in 20 minutes and 3 ml of t-butylperoxy pivalate was then added to the vinylpyrrolidone/water mixture through one of the necks of the flask. The temperature of the reactor was then maintained at 55° C. for 3 hours after which the system was heated to 80° C. in one-half hour and maintained at 80° C. for another 15 minutes. The reactor was then cooled to room temperature and the product discharged. The product had the following properties.

| Density | 0.8493 gm/ml |
|---|---|
| K value | 91.1 |
| APHA color | 5/10 |
| vinylpyrrolidone | 0.054 wt % |

Example 4

The procedure of Example 1 was followed using 2,2'-azobis(isobutyronitrile) as the initiator with similar results.

Example 5

The procedure of Example 1 is followed using hydrogen peroxide-potassium persulfate redox catalyst with similar results.

Example 6

The procedure of Example 1 was followed using t-butylperoxy benzoate. The PVP polymer obtained (K-90) had a relatively poorer water dissolution than the PVP polymer of Example 1.

Example 7

A. Pharmaceutical tablets were prepared using acetaminophen as the active ingredient and 1% and 2% by weight of the PVP K-90 powder prepared as in Example 1. The tablet was immersed in water and the amount of tablet dissolved with time was determined.

B. A similar pharmaceutical tablet was prepared using K-90 PVP prepared using the t-butylperoxy benzoate initiator of Example 6.

The tablets thus prepared were compared with respect to water dissolution at various periods of shelf-life. The analytical data reported in Tables 1 and 2 of the specifications for pharmaceutical tablets made with PVP prepared using t-amylperoxy pivalate or t-butylperoxy benzoate as initiator were obtained on (a) 6 tablets per test, repeated 3 times each test; (b) means standard deviations of ±3; and (c) a statistical level of significance of 99+%. The results are shown in Tables 1 and 2 below.

TABLE 1*

| Ex. No. | Shelf-Life (months) | Total % of Tablet Dissolved Immersion Time (min) | | | | |
|---|---|---|---|---|---|---|
| | | 60 | 120 | 180 | 240 | 300 |
| 7-A | 0 | 36.4 | 52.8 | 63.0 | 70.4 | 77.0 |
| 7-B | 0 | 33.6 | 50.4 | 61.1 | 68.9 | 75.4 |
| 7-A | 1 at 45° C. | 33.0 | 49.7 | 60.8 | 68.8 | 75.1 |
| 7-B | 1 at 45° C. | 30.4 | 46.3 | 56.3 | 63.8 | 69.6 |

*1% PVP level

TABLE 2*

| Ex. No. | Shelf-Life (months) | Total % of Tablet Dissolved Immersion Time (min) | | | | |
|---|---|---|---|---|---|---|
| | | 60 | 120 | 180 | 240 | 300 |
| 7-A | 0 | 43.9 | 63.8 | 74.7 | 80.7 | 84.9 |
| 7-B | 0 | 33.8 | 55.4 | 65.3 | 71.1 | 75.5 |
| 7-A | 1 at 45° C. | 42.5 | 59.3 | 69.1 | 76.1 | 81.1 |
| 7-B | 1 at 45° C. | 38.9 | 56.0 | 65.3 | 71.1 | 75.5 |

*2% PVP level

The results shown in Tables 1 and 2 demonstrate that pharmaceutical tablets made with PVP prepared using t-amylperoxy pivalate as initiator dissolved in water at a significantly greater rate, e.g., after 1 month at 45° C., than similar tablets prepared using PVP binders made from t-butylperoxy benzoate initiated polymerizations.

Example 8

The comparative experiments of Example 7 were repeated using hydrochlorothiazide as the active pharmaceutical ingredient in the tablet. Similar results were obtained with respect to dissolution rate of the tablet in water.

Example 9

Comparative experiments also were carried out using acetylsalicylic acid, chloramphenicol, chlorpromazine, methyl paraben, sulfathiazole, trimethoprim, and various other non-sterioidal anti-inflammatory drugs as the active pharmaceutical ingredients at 1 and 2% levels in place of acetaminophen in Examples 7A and 7B. Similar differences in dissolution rates were obtained.

While the invention has been described with particular reference to certain embodiments thereof, it will be understood that changes and modifications may be made which are within the skill of the art. Accordingly, it is intended to be limited by the appended claims only, in which:

What is claimed is:

1. A pharmaceutical tablet having a predetermined dissolution rate upon a given shelf-life consisting essentially of an active pharmaceutical ingredient and PVP as a binder therefor, said PVP being prepared by polymerizing vinyl pyrrolidone in the presence of a polymerization initiator selected from the group consisting of a peroxyester free radical initiator whose thermal homolysis reaction provides free radicals which are weak hydrogen abstractors, an axo initiator, and a redox initiator, and said PVP is characterized by being a linear, non-crosslinked polymer which is water soluble, wherein said PVP has a residual initiator level of less than 500 ppm achieved without crosslinking by heat decomposition of the initiator after polymerization.

2. A pharmaceutical tablet according to claim 1 wherein said initiator is a peroxyester initiator.

3. A pharmaceutical tablet according to claim 2 wherein said peroxyester is t-amylperoxy pivalate.

4. A pharmaceutical tablet according to claim 1 wherein said PVP has a K-value of 30 to 120.

5. A pharmaceutical tablet according to claim 1 wherein said PVP is present at a level of about 0.5-10% by weight in said tablet to provide such binder function.

6. A pharmaceutical tablet according to claim 1 wherein said initiator is an azo initiator.

7. A pharmaceutical tablet according to claim 1 wherein said initiator is a redox initiator.

8. A pharmaceutical tablet according to claim 1 wherein said active pharmaceutical ingredient is selected from the group consisting of chloramphenicol, chlorpromazine, methylparaben, sulfathiazole, trimethoprim, acetaminophen, and a non-steroidal anti-inflammatory agent.

9. A pharmaceutical tablet according to claim 1 wherein said PVP polymerization is carried out in water at a reaction temperature of about 56°-59° C., and said initiator is present in an amount of about 0.1 to 10% by weight of vinylpyrrolidone monomer present.

10. A pharmaceutical tablet according to claim 8 wherein said initiator level during polymerization of PVP is about 0.5 to 2%.

11. A pharmaceutical tablet according to claim 1 wherein the PVP used therein has a K-value of about 85 to 95.

12. A pharmaceutical tablet having a predetermined dissolution rate upon a given shelf-life consisting essentially of an active pharmaceutical ingredient and PVP as a binder therefor, said PVP being prepared by polymerizing vinyl pyrrolidone in the presence of a polymerization initiator selected from the group consisting of a peroxyester free radical initiator whose thermal homolysis reaction provides free radicals which are weak hydrogen abstractors, an azo initiator, and a redox initiator, and said PVP is characterized by being a linear, non-crosslinked polymer which is water soluble, wherein said PVP has a residual initiator level of less than 500 ppm achieved without crosslinking by decomposition of the initiator after polymerization, and wherein said PVP is subjected to a post-heat treatment at about 60°-85° C. to reduce the initiator level to less than 500 ppm.

* * * * *